United States Patent [19]

Rogachev et al.

[11] 4,352,065
[45] Sep. 28, 1982

[54] NONDESTRUCTIVE ELECTROMAGNETIC INSPECTION OF PIPELINES INCORPORATED IN AN ELECTRICALLY CLOSED LOOP

[76] Inventors: Viktor I. Rogachev, Jurievsky pereulok, 22 korpus 2, kv. 55; Lev I. Trakhtenberg, Proletarsky prospekt, 54, kv. 39; Petr N. Shkatov, ulitsa Musy Dzhalilya, 17, korpus 1, kv. 127, all of Moscow, U.S.S.R.

[21] Appl. No.: 31,484

[22] Filed: Apr. 19, 1979

[30] Foreign Application Priority Data

Apr. 28, 1978 [SU] U.S.S.R. ................ 2604876
Apr. 28, 1978 [SU] U.S.S.R. ................ 2604877

[51] Int. Cl.³ .................. G01N 27/82; G01R 33/12
[52] U.S. Cl. ........................ 324/238; 324/220; 324/240
[58] Field of Search ............ 324/200, 219–221, 324/260, 261, 51, 204, 209, 211, 222, 227–229, 232, 233, 234–243, 262

[56] References Cited

U.S. PATENT DOCUMENTS

| | | | |
|---|---|---|---|
| 1,743,318 | 1/1930 | Carrington | 324/52 |
| 2,650,344 | 8/1953 | Lloyd | 324/260X |
| 2,788,486 | 4/1957 | Guggi | 324/51 |
| 2,980,850 | 4/1961 | Cochran | 324/242 |
| 3,166,710 | 1/1965 | Schmidt | 324/242 |
| 3,427,872 | 2/1969 | Leep et al. | 324/209 X |
| 3,539,915 | 11/1970 | Walters et al. | 324/220 |
| 3,693,075 | 9/1972 | Forster | 324/220 X |
| 3,719,883 | 3/1973 | Pentecost | 324/51 |
| 3,783,370 | 1/1974 | Birdwell et al. | 324/243 |
| 3,875,502 | 4/1975 | Neumaier | 324/241 |
| 3,916,302 | 10/1975 | Madewell | 324/220 |
| 3,944,911 | 3/1976 | Tornblom | 324/242 |
| 4,088,952 | 5/1978 | Sikora | 324/239 |

*Primary Examiner*—Gerard R. Strecker
*Attorney, Agent, or Firm*—McAulay, Fields, Fisher, Goldstein & Nissen

[57] ABSTRACT

The method according to the invention comprises producing an alternating magnetic flux coupled to an electrically closed loop which includes a pipeline to be checked, and measuring at least on electromagnetic field parameter over the whole length and perimeter of the pipeline. The distribution function of the electromagnetic field parameter thus obtained is indicative of the state of the pipeline. The method is more effective than the conventional techniques in that it ensures a more uniform spreading of current over the pipeline, in that it makes possible to inspect hard-to-get-at portions of pipelines without installing magnetic flux excitation means at those portions, and in that it rules out the effects of the magnetic flux on the output signals of measuring transducers. The invention is further concerned with a device for nondestructive inspection of pipelines primarily, pipelines, of atomic power stations. The device according to the invention comprises one or more closed magnetic circuits, each intended to accommodate a portion of a pipeline or portions of a number of pipelines for checking purposes. Portions of the magnetic circuits are encompassed by exciting coils. The device further incorporates an a.c. source, a system of inductance coils, a system of magnetic field measuring transducers, a communication link, a unit for processing signals arriving from the magnetic field measuring transducers, and a data presentation unit.

30 Claims, 7 Drawing Figures

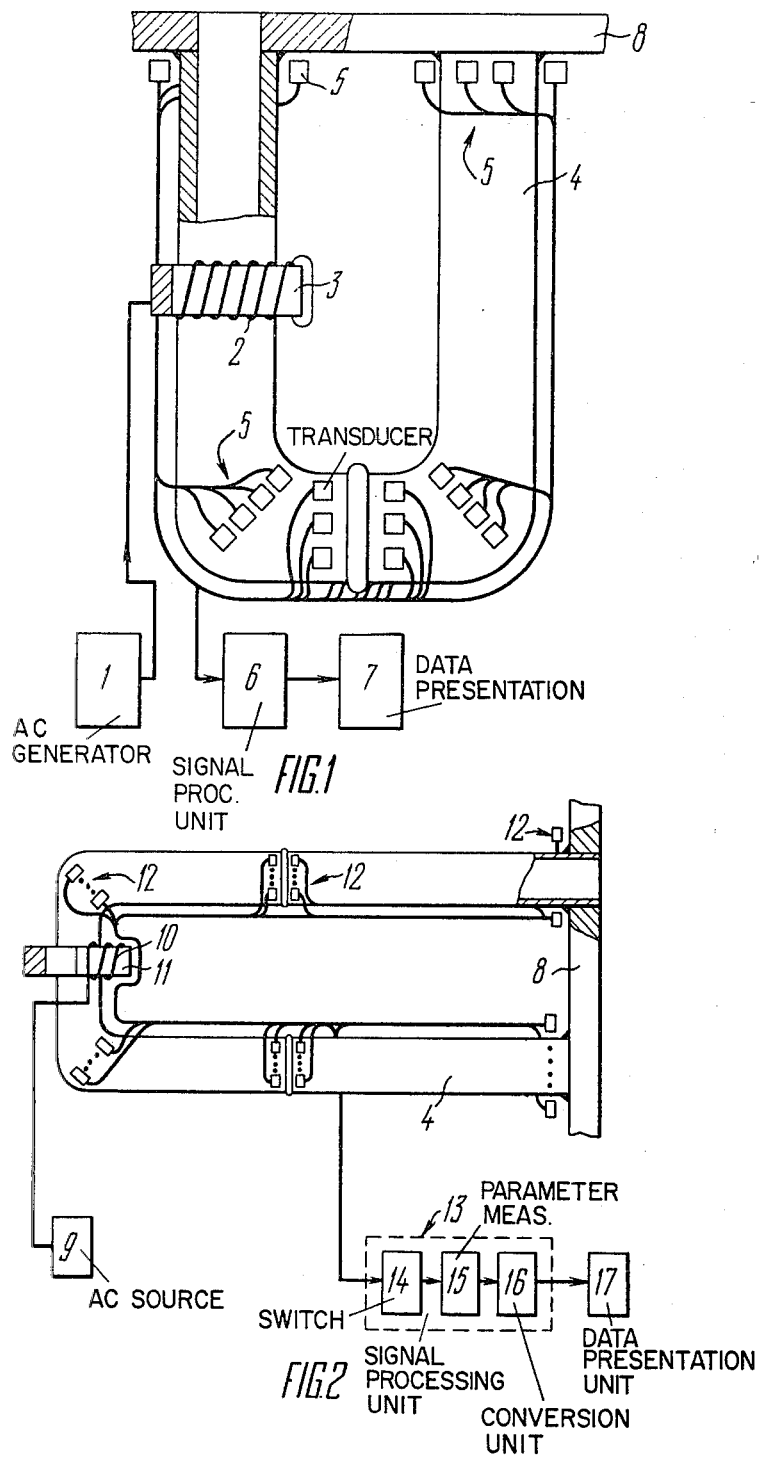

NONDESTRUCTIVE ELECTROMAGNETIC INSPECTION OF PIPELINES INCORPORATED IN AN ELECTRICALLY CLOSED LOOP

FIELD OF THE INVENTION

The present invention relates to the nondestructive inspection of pipelines and, more specifically, to a method for nondestructive inspection of pipelines and a device for carrying out that method.

The invention is applicable to nondestructive inspection of electrically conducting objects which make up one or more electrically closed loops or are portions thereof, such as pipelines of atomic power stations.

The invention is best suited for running and periodical checks of pipelines of atomic power stations at points of utmost mechanical stresses, such as bends, welded joints, etc.

The invention is also advantageous for checking electrically conducting objects which make up an electrically closed loop or are portions thereof, such as oil pipelines or sheaths of the control and safety system at an atomic power station.

BACKGROUND OF THE INVENTION

There is known a method for nondestructive inspection of atomic reactor pipelines, whereby pipeline portions to be inspected are connected to the arms of a bridge, whereupon alternating current is passed through the pipeline by an appropriate means electrically connected thereto; the degree of unbalance of the bridge is indicative of flaws in the pipeline portions being checked.

However, an unbalance of the bridge can only be observed in cases of major flaws. Minor flaws account only for negligible changes of the impedance which are commensurable with interfering factors, such as the temperature gradient between the pipeline portions connected to the arms of the bridge.

The method under review is disadvantageous in that it requires a great number of electric connections to the pipeline portions being inspected. Being a complication in itself, this also affects the accuracy of checking, especially in view of variable thermal and chemical conditions under which a pipeline normally operates.

The method does not make it possible to pinpoint the cause of an output signal. Signals of an equal magnitude may be caused by a single major defect or by a number of minor defects. There are cases when a reactor has to be shut down because of an inaccurate inspection.

True, the method does make it possible to establish the presence of a defect in a pipeline, but the exact location of the defect remain unknown.

There is further known a method for nondestructive inspection of pipelines, which consists in producing an alternating magnetic flux to interact with the wall of the pipeline, and measuring the parameters of the magnetic field brought about by eddy currents produced in the pipeline wall. The magnitude of the output signal of the measurement device is indicative of the state of the pipeline in the zone of interaction between the pipeline wall and the magnetic flux.

However, this latter method is not accurate enough. First, it is not sensitive enough to defects found deep inside the pipeline wall. Second, the method does not provide for a sufficiently high accuracy of measuring the parameters of the magnetic field produced by the eddy currents, keeping in mind that the magnetic field caused by the eddy currents has to be discriminated from the total magnetic field produced by both eddy currents and alternating magnetic flux.

There is further known a method for nondestructive inspection of pipelines (cf. U.S. Pat. No. 3,875,502 of 1975), which consists in using an alternating magnetic flux to produce an electromagnetic field and measuring the distribution of at least one parameter of the electromagnetic field in the zone of electromagnetic interaction between the magnetic flux and the pipeline. The distribution function of at least one electromagnetic field parameter, which is thus produced, is indicative of the state of the pipeline.

Like the previously discussed methods, this method lacks accuracy. This is due to the necessity of dscriminating the eddy current magnetic field from the total magnetic field, as well as to the strong nonuniformity of the total magnetic field. Besides, the method can hardly lend itself to the inspection of hard-to-get-at pipeline portions, especially at places where the pipeline is connected to other equipment, as well as at bends, at the locations of supporting structures, etc. The reason is the necessity of using exciting coils which envelop the pipeline in the inspection zone.

There is known a device for nondestructive inspection of pipelines, comprising means to supply alternating currents and voltages, means to connect them to the pipeline and thus produce a closed electric loop, and means for measuring electric characteristics of that loop for each frequency.

The measuring means is an impedance bridge whereof two arms are connected to portions of the pipeline that are to be inspected. The electric characteristic of the loop, which is to be measured, is the impedance of that loop.

However, the device under review does not make it possible to detect flaws at an early stage of their development, because such flaws can only be detected in the case of a significant change of the electric characteristics of the closed electric loop. Thus the device can only detect sufficiently serious damages.

Besides, the inspection of different sections of a pipeline requires a great number of electric connections between said connection means and the pipeline, which is not an easy task to perform, considering variable temperature and chemical conditions under which an atomic reactor pipeline normally operates.

The device cannot say if an output signal is caused by a single major defect or a plurality of minor defects. Thus a reactor shut-down and ensuing losses may happen without any real reason at all.

In order to pinpoint the location of a defect, the device in question must obviously be complemented with other devices, such as ultrasonic flaw detectors which necessitate a shut-down of the reactor to be put into operation.

Finally, it is impossible to inspect those points of the pipeline where it is connected to the measuring means.

There are further known devices for nondestructive inspection of pipelines of the type that comprises an a.c. source, a system of eddy current transducers of the kind that has to be put on the surface of an object to be investigated, a communication line, a unit for processing output signals of the eddy current transducers, and a data presentation unit.

The device is not accurate enough, which is due to its low sensitivity to defects found deep inside the pipeline walls and a low signal-to-noise ratio in cases the primary detectors are displaced in the inspection zone.

There is further known a device for nondestructive inspection of pipelines (cf. U.S. Pat. No. 3,875,502 of 1975), comprising an a.c. source connected to exciting inductance coils which contact the surface of a pipeline to be checked and thus produce a uniform magnetic field over a portion of the pipeline's surface. The device further incorporates a system of magnetic field measuring transducers arranged within said magnetic field, in immediate proximity to the pipeline's surface. It also includes a signal processing unit, a data presentation unit and a communication link to connect the system of magnetic field measuring transducers to the data processing unit, as well as to connect an inductance coil excitation means to said inductance coils. The a.c. source supplies alternating current which is passed through the inductance coils, whereby an alternating magnetic flux is brought about, which goes through the pipeline portion to be checked and produces eddy currents therein. The magnetic field measuring transducers are measuring inductance coils. These are arranged so that their axes are perpendicular to the magnetic lines, which rules out any electromagnetic interaction between the exciting coils and measuring inductance coils. A defect in the pipeline alters the eddy currents distribution and thus changes voltage across the measuring coils which interact with the eddy currents. The change of voltage is converted by the unit for processing the output signal of the magnetic field measuring transducers and recorded by the data presentation unit.

The latter device, too, is not accurate enough, which is due to a low signal-to-noise ratio because of possible displacements of the measuring transducers in the checking zone, as well as strong effects of electrically conducting objects, such as pipeline supports, on the results of measurements. The accuracy of inspection is also affected by different sensitivity of the measuring transducers to non-uniformities of the pipeline, and their low sensitivity to defects like transverse cracks which are most likely to occur in welds. Another reason for the low accuracy of checking the pipeline condition is the non-uniformity of eddy currents produced in the pipeline.

Finally, the device is such that the exciting coils have to be arranged right in the inspection zone, which makes the device too complicated and the inspection of hard-to-get-at places inconvenient.

SUMMARY OF THE INVENTION

It is an object of the present invention to improve the accuracy of nondestructive inspection of pipelines which form one or more electrically closed loops or are portions of such loops.

The invention consists in coupling an alternating magnetic flux to at least one of said loops, which is followed by measuring at least one electromagnetic field parameter along the entire length and perimeter of the pipeline or over its portions within the zone of electromagnetic interaction between the pipeline and the alternating magnetic flux, so as to produce a distribution function of at least one electromagnetic field parameter.

If it is possible to arrange the magnetic field transducers inside the pipeline, it is best that the distribution function of at least one parameter of the magnetic field produced by the magnetic flux coupled to the electrically closed loop should be measured inside the pipeline.

In the case of inspecting pipelines enveloping a portion of the electrically closed loop and incorporated in that loop, it is best that the distribution function of at least one parameter of the magnetic field produced by the magnetic flux coupled to the electrically closed loop should be measured over the external surface of that portion of the pipeline.

In the case of inspecting ferromagnetic pipelines or pipelines having welded joints comprising ferromagnetic components; it is best to measure magnetic noise and obtain the distribution function of at least one magnetic noise parameter, which would be indicative of the condition of the pipeline.

It is further advisable to measure the distribution of at least one magnetic field parameter on the internal and external surfaces of the pipeline and over the entire length and perimeter of the pipeline or portions thereof and thus obtain the distribution function of at least one magnetic field parameter.

In the case of inspecting operating pipelines, it is recommended to measure variations with time of at least one distribution function of at least one parameter of physical processes going on in the pipeline as a result of its interaction with the alternating magnetic flux, which variations are indicative of the state of the pipeline.

The change with time of the distribution function of magnetic field parameters makes it possible to detect non-uniformities in an operating pipeline.

The invention further consists in providing a device for nondestructive inspection of pipelines, comprising an a.c. source, exciting inductance coils, magnetic field measuring transducers, a communication link, a unit for processing output signals of the magnetic field measuring transducers, and a data presentation unit, which device is provided, according to the invention, with one or more closed magnetic circuits, each accommodating a portion of a pipeline or portions of a number of pipelines to be inspected, the exciting inductance coils enveloping portions of the magnetic circuits.

The inspection is more effective if the magnetic circuits are of the split type.

Also, the inspection would be more effective if the device includes a measuring inductance coil encompassing the pipeline, a voltage measuring unit and an indicator, the measuring inductance coil being connected to the voltage measuring unit whose output is connected to the indicator.

The inspection would likewise be more effective if the device includes at least one unit for integral estimation of the properties of a closed loop branch being checked, which unit comprises measuring transducers whereof each incorporates a closed magnetic circuit, an inductance coil encompassing a portion of that magnetic circuit, and a current meter with an indicator, the inductance coils of the transducers being connected to the current meter.

The effectiveness of the invention would be further improved if the device is provided with an automatic control system to control current flowing through a portion being checked of a pipeline which is incorporated in one or more branches of an electrically closed loop, which system comprises at least one magnetic field measuring transducer which is a closed magnetic circuit whereof a portion is encompassed by an inductance coil, a current meter with an indicator, a current setting unit, a switch, and a comparator whereof a first input is connected via the switch to the inductance coils of the respective magnetic field transducers, whereas its second input is connected to the current setting unit, an output of the comparator being connected to an a.c. source of the controlled type.

In order to detect flaws in pipelines of ferromagnetic materials or materials comprising ferromagnetic components, it is necessary that the device should include a magnetic noise processing unit having its input connected to the magnetic field measuring transducers and its output connected to the data presentation unit.

In order to obtain a distribution function of magnetic fields produced by the current passed through the pipeline over the entire length and perimeter of the pipeline, it is necessary that the device should be provided with a system for a transfer of the measuring transducers inside the pipeline.

In order to obtain a distribution function of magnetic fields produced by the current passed through the pipeline over the entire length and perimeter of the pipeline, it is necessary that the device should be provided with a system for a transfer of the measuring transducers over the external surface of the pipeline.

In order to make it possible to inspect operating pipelines, it is desirable that the units for processing output signals of the magnetic field measuring transducers should be capable of storing information and calculating its changes with time.

The invention accounts for a high accuracy of nondestructive inspection of electrically conducting objects making up a closed loop or being part of such a loop, primarily, pipelines of atomic power stations.

BRIEF DESCRIPTION OF THE ACCOMPANYING DRAWINGS

Other objects and advantages of the present invention will become more apparent from the following detailed description of preferred embodiments thereof, taken in conjunction with the accompanying drawings, wherein:

FIG. 1 is a schematic illustration of the inspection of a pipeline which forms an electrically closed loop or is part of such a loop, in accordance with the invention;

FIG. 2 is a schematic view of a device for nondestructive inspection of pipelines which form electrically closed loops and/or are parts of such loops, in accordance with the invention;

DETAILED DESCRIPTION OF THE INVENTION

Figure 3:
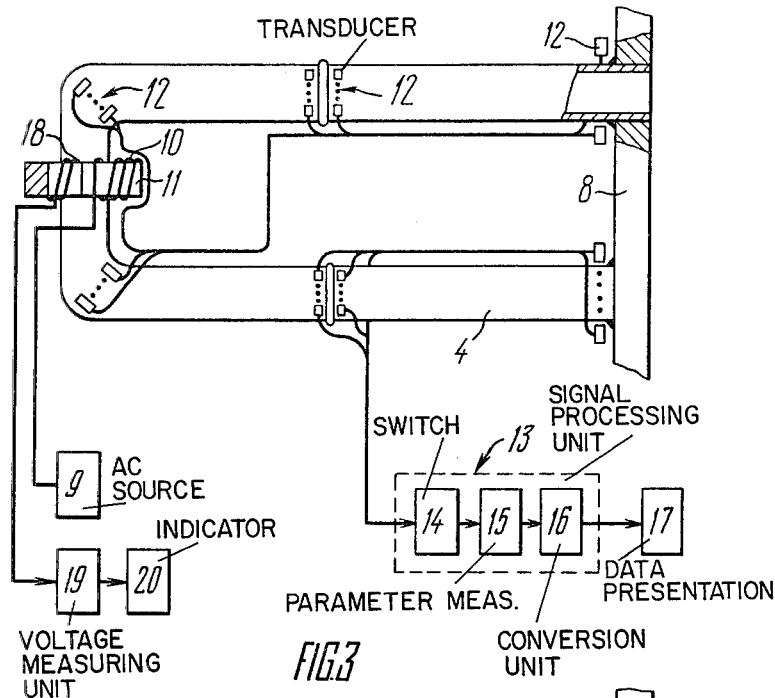
FIG. 3 is a schematic view of a device for nondestructive inspection of pipelines which form electrically closed loops and/or are parts of such loops, which device is capable of integral estimation of the state of a pipeline, in accordance with the invention.

The method according to the invention is illustrated by the following description of a system for nondestructive inspection of pipelines which form an electrically closed loop and/or are parts of such a loop.

The system comprises an a.c. generator 1 (FIG. 1) and an exciting inductance coil 2 wound around a closed magnetic circuit 3 which encompasses a portion of a pipeline 4. The system further includes a group of primary detectors or transducers, 5 which are sensitive to at least one magnetic field parameter.

The transducers 5 are spaced over the length and perimeter of the pipeline 4 and are concentrated at places of utmost mechanical stresses, such as bends, welded joints, etc. A communication link connects the transducers 5 to a signal processing unit 6 connected, in turn, to a data presentation unit 7.

In combination with a plate 8, the pipeline 4 forms a closed loop.

The method according to the invention is carried out as follows.

The a.c. generator 1 supplies alternating current which is passed through the exciting inductance coil 2 to produce a magnetic flux concentrated in the closed magnetic circuit 3 and coupled to the electrically closed loop formed by the pipeline 4 to be checked and the plate 8 welded to the pipeline 4. The loop is closed, which is the reason why currents are produced therein and circulate along the pipeline 4. The electromagnetic field produced over the length and perimeter of the pipeline 4 is only caused by these circulating currents whose direction is such as to make it easy to detect the most probable defects found along the welded joints.

The magnitude of at least one electromagnetic field parameter, such as the magnetic field strength modulus, is recorded by the magnetic field measuring transducers 5.

Naturally, the transducers 5 must be sensitive to magnetic field parameters. The function of the transducers 5 may be performed by inductance coils, magnetoresistors, ferroprobes, etc.

Output signals of the measuring transducers 5 are sent through the communication link to the input of the signals processing unit 6, wherefrom they are applied to the data presentation unit 7. The signals processing unit 6 is capable of data conversion and storage, which provides information on the distribution function of the parameters being measured, as well as information on variations of that function with time. These are factors which are conducive to a better accuracy of checking. The accuracy of inspection is improved by installing the measuring transducers 5 inside the pipeline 4, in which case the output signals of the transducers 5 only depend on the non-uniformity of the cross-sectional shape and electrophysical properties of the pipeline 4. The reason is this: if the pipe is symmetrical, there is no magnetic field inside it, because current flows along the pipe.

In the case of inspecting objects which form a coaxial system or a part thereof, the accuracy of checking the external pipeline 4 is improved by measuring the distribution function of electromagnetic field parameters with the aid of transducers 5 mounted on the surface of the external pipeline 4. A magnetic field is produced around the external pipe of the coaxial system only if that pipe has some defects or non-uniformities. The output signal of the transducers 5 is only dependent on non-uniformities in that pipe, but does not vary if the transducers 5 are moved along a uniform pipeline 4.

The parameters of defects will be assessed more accurately from the distribution functions of electromagnetic field parameters if the generator 1 is of the multifrequency type and produces currents of different frequencies in the pipeline 4, which penetrate to different depths.

In the case of inspecting pipelines 4 of ferromagnetic materials or composite materials comprising ferromagnetic components, which may be found, for instance in welded joints, the transducers 5 may be used to detect Barkhausen discontinuities. The output signals of the transducers 5 are processed as described above. The improved accuracy of inspection is due to the fact that Barkhausen discontinuities are highly dependent on variations in the structure of ferromagnetic materials.

The effects of non-uniformities in the structure of metal of the pipeline 4 can be ruled out by measuring the variations with time of the distribution functions of electromagnetic field parameters. This is done by storing output signals of the transducers 5 and measuring these signals again after a specified time interval. The change of these signals is indicative of the condition of the pipeline 4.

The invention is further concerned with a device for carrying out the foregoing method for nondestructive inspection of pipelines. The device comprises a conventional a.c. source 9 (FIG. 2) whose output is connected to an exciting inductance coil 10 which encompasses a portion of a closed magnetic circuit 11. The latter has a window sufficiently large to accommodate a portion of the pipeline 4 to be checked. The closed magnetic circuit 11 is split if it has to be used for the inspection of pipelines 4 incorporated in independent loops. Thus the magnetic circuit 11 is easy to install and dismantle, which helps to speed up the inspection. The device further includes magnetic field measuring transducers 12 of the concentric type, such as inductance coils. The transducers 12 are mounted on portions of the pipeline 4 to be checked and connected by a communication link to a signal processing unit 13. The latter comprises a switch 14, a unit 15 for measuring parameters of output signals of the measuring transducers 12, and a data storage and conversion unit 16; all these units are of the conventional type. In the simplest case, the switch 14 is an operator-controlled switch, although it is preferable to use automatic switches, such as conventional contactless switches operated by a ring counter. In the simplest case, the unit 15 for measuring parameters of output signals of the measuring transducers 12 is a conventional voltmeter, power factor indicator or oscillograph. In the simplest case, the data storage and conversion unit 16 is the memory of a storage oscillograph, although a digital computer is recommended in view of an extensive amount of information obtained in the course of inspection. In this case the parameters of variable signals should be measured by a conventional digital voltmeter or a conventional digital power factor indicator. The signal processing unit 13 is connected to a data presentation unit 17 which in the simplest case is a conventional recorder or a conventional audio or light warning device. If a digital computer is incorporated in the device, it is preferable that the computer's peripherals should be employed for the display of data. In this case the data presentation unit 17 may be a numeric printer, a cathode ray tube or a plotter.

In the simplest case, the integral estimation of the entire electrically closed loop can be effected by using a measuring inductance coil 18 mounted on the closed magnetic circuit 11 and intended to measure the magnetic flux through said closed magnetic circuit 11 (FIG. 3). The coil 18 is connected to a voltage measuring unit 19, such as a voltmeter. The latter is, in turn, connected to a conventional indicator 20.

Figure 4:
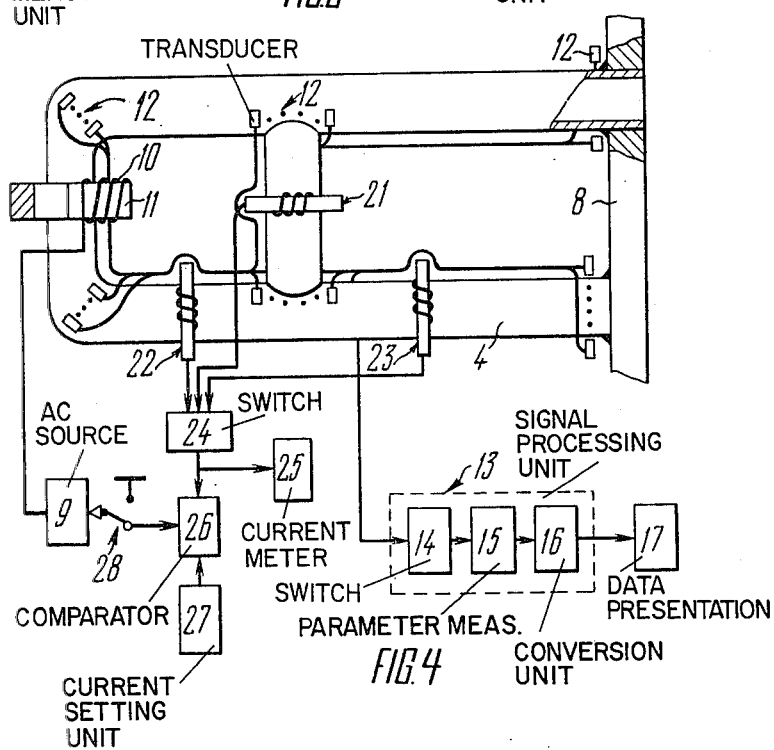
FIG. 4 is a schematic view of a device for nondestructive inspection of manifolds which form electrically closed loops and/or are parts of such loops, in accordance with the invention.

For the inspection of pipelines 4 (FIG. 4) which form several electrically interconnected loops, the device according to the invention is provided with a unit for integral estimation of the properties of the branch to be checked, which unit comprises magnetic field measuring transducers 21,22 and 23. Each of these comprises, in turn, a closed magnetic circuit encompassed by an inductance coil, as well as a switch 24, and a current meter 25 with an indicator.

The foregoing integral estimation unit is also used in a system for automatically controlling the intensity of current through a portion of the pipeline 4 being checked, which is incorporated in one or more branches of the closed loop. The automatic current control system further includes a comparator 26, a current setting unit 27 and a switch 28. In this case the a.c. source 9 is of the controlled type.

In the course of pipeline inspection, the magnetic field measuring transducers 21, 22 and 23 and envelop portions of closed loops and are connected via the switch 24 to the current meter 25 comprising an indicator means, such as an ammeter. The switch 24 has its input connected to a first input of the comparator 26 whose second input is connected to the current setting unit 27. The output of the comparator 26 is connected via a switch 28 to a control input of the a.c. source 9.

Figure 5:
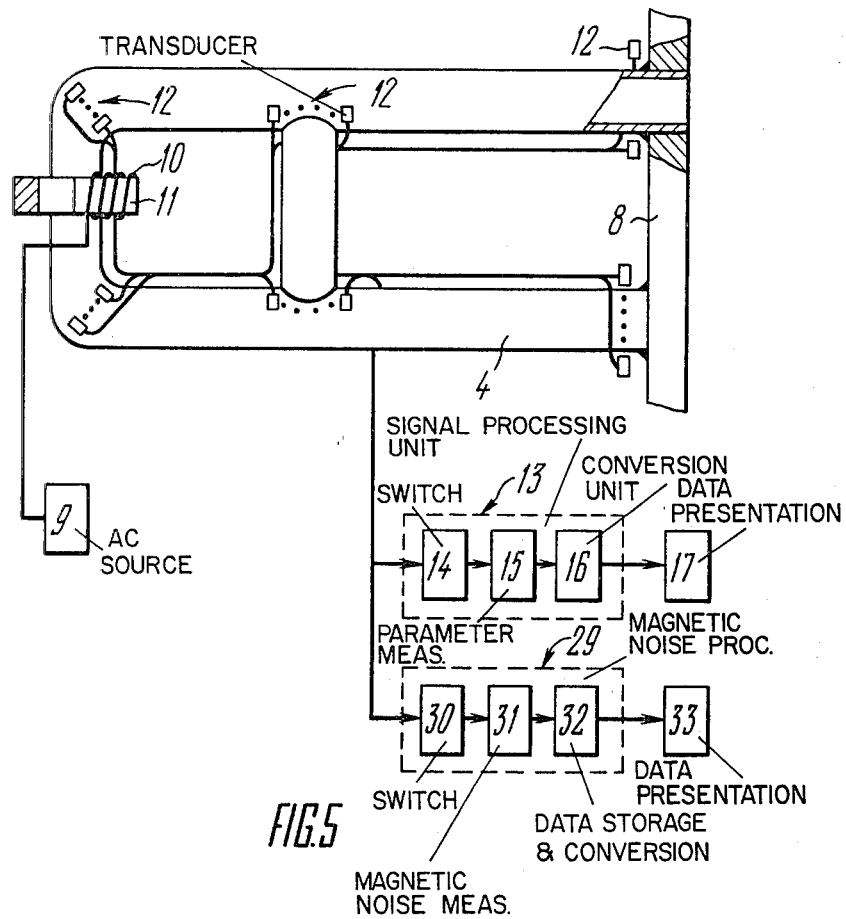
FIG. 5 is a schematic view of a device for nondestructive inspection of pipelines which form electrically closed loops and/or are parts of such loops and which are of ferromagnetic materials or materials containing ferromagnetic components, in accordance with the invention.

For the inspection of pipelines 4 of ferromagnetic materials or pipelines 4 having portions with ferromagnetic components, such as welded joints, the device in accordance with the invention is provided with a unit 29 (FIG. 5) for processing signals carrying information on magnetic noise, or Barkhausen discontinuities. The signals processing unit 29 comprises a switch 30 whose inputs are connected to the magnetic field measuring transducers 12 arranged over those portions of the pipeline 4 which contain ferromagnetic components; the unit 29 further includes a unit 31 for measuring magnetic noise parameters, and a data storage and conversion unit 32. The signals processing unit 29 is connected to a data presentation unit 33. The unit 31 for measuring magnetic noise parameters is of the conventional type. The switch 30, the data storage and conversion unit 32 and the data presentation unit 33 are similar to the aforementioned units 24, 15 and 16, respectively.

Figure 6:
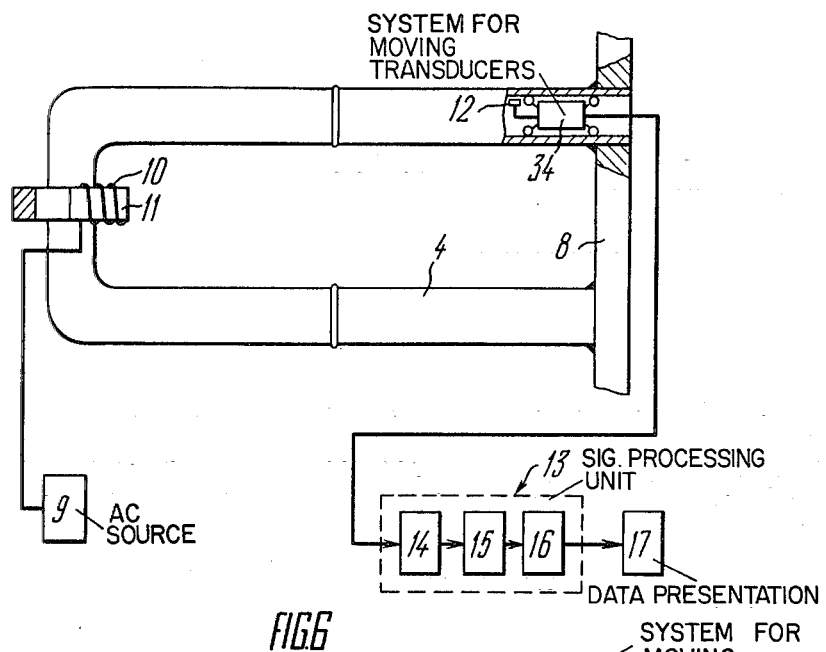
FIG. 6 is a schematic view of a device for nondestructive inspection of pipelines forming an electrically closed loop and/or being parts of such loops, the inspection comprising the scanning of the internal surface of the pipeline and requiring a shut-down of the reactor, in accordance with the invention.

With the reactor being shut down, it is possible to check all the metal of the pipeline 4 (FIG. 6). With this aim in view, the device according to the invention is additionally provided with a system 34 for moving the magnetic field measuring transducers 12 inside the pipeline 4.

Figure 7:
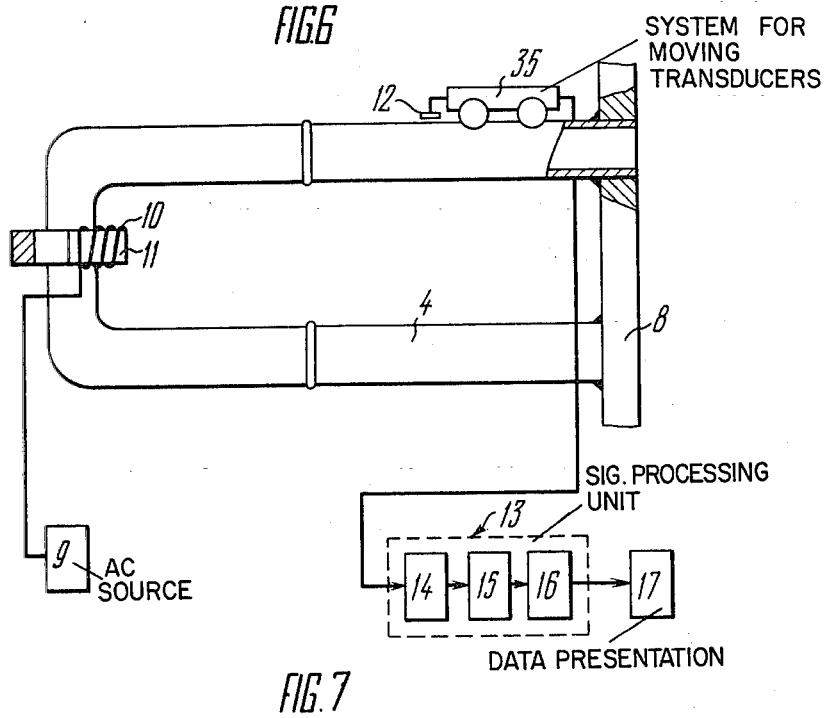
FIG. 7 is a schematic view of a device for nondestructive inspection of pipelines accessible from the outside and forming an electrically closed loop and/or being parts of such a loop, the inspection comprising the scanning of the external surface of the pipeline, in accordance with the invention.

To ensure a maximum accuracy of inspection of the external surface of the pipeline 4 (FIG. 7), the device according to the invention is additionally provided with a system 35 for moving the magnetic field measuring transducers 12 over the external surface of the pipeline 4.

The device according to the invention may incorporate the current setting unit 27 and comparator 26 of the type described in the book by I. M. Bolotin and V. A. Pavlenko "Porogovye ustroystva dlya priborov avtomaticheskogo controlya i regulirovaniya"/"Threshold Devices for Automatic Control Means"/, Energia Publishers, Moscow, p. 83. The magnetic noise parameter measuring unit 31 may be of the type described in the journal "Defectoscopia", No.4, 1977. The systems 34 and 35 (FIGS. 6 and 7, respectively) for moving the magnetic field measuring transducers 12 may be of the type described in the article by Brodsky et al., "Defectoscopia metalla oborudovaniya atomnykh electrostantsiy pri expluatatsii"/"Detection of Flaws in Metal of Atomic Power Station Equipment in the Course of Operation"/, the journal "Atomnaya energia"/"Atomic Energy"/, Vol. 42, Series 1, 1977).

The device according to the invention operates as follows.

A portion of the pipeline 4 (FIG. 2) to be checked is encompassed by the closed magnetic circuit 11. The a.c. source 9 applies current to the exciting inductance coil 10 which encompasses the closed magnetic circuit 11. Thus there is produced an alternating magnetic flux concentrated in the closed magnetic circuit 11 and coupled to the electrically closed loop formed by the pipeline 4 and the plate 8 welded to said pipeline 4. The electromagnetic interaction between the magnetic flux and the electrically closed loop produces electric current which flows along the pipeline 4. The current density distribution in the pipeline 4 is determined by the frequency of the alternating current produced in said pipeline 4 and by the electrophysical properties of the material of said pipeline 4. Apparently, defects of the structure or discontinuities in the pipeline 4 lead to variations in the magnitude and density of the current induced in said pipeline 4. This, in turn, changes the magnetic field around the pipeline 4, produced by the current through said pipeline 4. The result is a change of the output signals of the magnetic field measuring transducers 12. The signals processing unit 13 measures changes in the output signal parameter which is the most sensitive to defects in the object of inspection; this parameter may be the amplitude of the signal, for example. The output signal of the data presentation unit 17 is indicative of the presence and scope of defects in the pipeline 4.

The nondestructive inspection process consists in measuring parameters of output signals of the magnetic field measuring transducers 12 by the signals processing unit 13. For this purpose, the signals processing unit 13 is connected to the transducers 12 via the switch 14. In the simplest case, the switching sequence may be set by the operator; it may also be set and controlled by a computer.

The magnitudes of the output signals of the transducers 12 are stored. After a specified time interval, the measurement is repeated and the changes of the output signals due to magnetic field variations are recorded. The strength of the magnetic field is related to the properties of the material and, first of all, to the continuity of the pipeline 4. Thus variations in the magnitude of the output signals of the transducers 12 are indicative of cracks or some changes in the structure of the material of the pipeline 4. A comparison of signals of closely located transducers 12 makes it possible to establish the gradient of change of the magnetic field over the pipeline portion being checked. If the gradient is small, the most probable reason for the change of the output signals of the transducers 12 is a change in the structure of the material. Howevr, if the gradient is great, this is a clear indication of a crack. A study of the gradient of the change of output signals of the transducers 12 makes it possible to determine the length and orientation of the crack. The depth of a crack can be found by comparing the output signals of the transducers 12 at different frequencies of alternating current induced in the pipeline 4. An increased frequency of this current accounts for a concentration of current density in the surface layers of the material of the pipeline 4. Thus by varying the frequency of the a.c. source 9, one can vary the current distribution in the pipeline 4. This makes it possible to establish the depth of cracks or pits. If the depth of current penetration is less than the depth of a crack, there is no change in the recorded signal. Thus the depth of a crack can be found by registering the minimum frequency at which there is no change in the output signals of the magnetic field measuring transducers 12, and calculating the depth of current penetration at that frequency.

In the simplest case, signals can be stored and their change with time can be registered with the aid of a recorder or a storage oscillograph. However, it is best to use a computer which can process great amounts of data and store data over an unlimited length of time.

It is recommended that the magnetic field measuring transducers 12 should be arranged at those portion of the pipeline 4 where the probability of flaws is the highest. This primarily applies to bends and welded joints. However, in some cases cracks may develop at those portions of the pipeline 4 which are normally considered safe. Such cracks are due to hidden defects which had not been detected before the atomic power station was commissioned. It would be hardly rational to inspect the whole length of the pipeline 4 with the aid of magnetic field measuring transducers 12 mounted at different portions of said pipeline 4.

The rational approach would be to perform integral estimation of the entire electrically closed loop which also includes those pipeline portions that are not covered by the magnetic field measuring transducers 12. Integral estimation does not make it possible to detect flaws which are just beginning to emerge. However, it is useful in that it helps to detect major flaws and thus eliminate an accident. Obviously, the growth of a crack in the pipeline 4 incorporated in the electrically closed loop leads to a change of the resistance of the whole loop and a change of the current induced in that loop. The result will be a change of the magnetic flux through the closed magnetic circuit 11 and a change of voltage across the terminals of the measuring inductance coil 18 (FIG. 3). This change of voltage is registered by the voltmeter 19 and displayed by the indicator 20.

In the case of inspecting pipelines 4 which form several interconnected loops, it is recommended that integral estimation of individual loops should be performed separately. The result is a better accuracy and a surer detection of cracks. Integral estimation of the state of different loops is effected by monitoring the change of current through the loops, which is done by successively connecting the magnetic field measuring transducers 21, 22 and 23 (FIG. 4) via the switch 24, with the switch 28 being in its upper position, to the current meter 25 and recording its readings to compare them with the earlier readings. A digital ammeter is best for this purpose.

The magnetic field measuring transducers 12 are expected to display the same degree of sensitivity to defects of the same size. For this purpose, it is necessary to ensure equal current densities in the individual branches of the ramified electrically closed loop. This is done by means of automatic control of current by the controlled a.c. source 9. The current intensity at the output of the source 9 is determined by the output voltage of the comparator 26. The comparator 26 compares the magnitude of current set by the unit 27 with the current value in the branch of the pipeline 4 being checked. With the switch 28 in its lower position, the difference signal is applied to the input of the a.c. source 9. Thus the current in the branch being checked is automatically maintained at the prescribed level, wherefore the transducers 12 show the same sensitivity to flaws of the same size.

In the case of inspection of pipelines 4 of ferromagnetic materials or pipelines 4 having portions of material including ferromagnetic components, such as welds, the unit 29 (FIG. 5) for processing signals carrying information on magnetic noise comes into play to measure Barkhausen discontinuities. For this purpose, the switch 30 successively connects the magnetic field measuring transducers 12 to the unit 31 for measuring parameters of magnetic noise signals. The parameters of signals carrying information on magnetic noise are measured and compared to values stored by the data storage and conversion unit 32. The results of the comparison are displayed by the data presentation unit 33.

Whenever a more detailed study of the pipeline 4 is necessary, the magnetic field measuring transducers 12 are mounted on the scanning system 34 (FIG. 6) which is movable inside the pipeline 4. The transducers 12 may also be mounted on the scanning system 35 (FIG. 7) which is movable over the external surface of the pipeline 4.

In this case the inspection consists in moving the transducers 12 over the surface of the pipeline 4 and recording the results of measurements on a carrier, such as magnetic tape of the digital computer incorporated in the unit 13 for processing output signals of the magnetic field measuring transducers 12.

The values thus obtained are compared to the previous measurements, and the result of the comparison is displayed by the data presentation unit 17. However, major defects, which cause a signal of a higher value than signals caused, for example, by changes in the structure of the material of the pipeline 4, are detected and indicated even before the comparison is actually effected. Normally, the scanning of the external and/or internal surfaces of the pipeline 4 requires a shut-down of the reactor.

To summarize, the method and device according to the invention are highly effective for nondestructive inspection of pipelines of atomic power stations and steam stations, as well as for nondestructive inspection of any other objects that form a closed loop or are parts of such a loop.

The effectiveness of the method and device according to the invention is accounted for by the following factors:

the magnetic field, that induces currents in the pipeline 4, does not interact with the measuring transducers 12 which are sensitive to magnetic field parameters;

a single exciting coil 10 is used to excite currents over the entire length of the pipeline 4, which is especially important for the inspection of hard-to-get-at portions of the pipeline 4 and makes it possible to simplify the device for non-destructive inspection;

the direction of currents is the most convenient to detect defects of the most probable orientation, namely, transverse cracks;

the current distribution over the pipeline is quite uniform, which makes it possible to inspect pipeline portions next to branch pipes, supporting structures, etc.;

the effects of variations of electromagnetic parameters of the pipeline on the detectability of flaws, such as discontinuities, are reduced due to the elimination of the effects of these parameters on the magnetic flux.

What is claimed is:

1. A method for nondestructive inspection of a pipeline incorporated in an electrically closed loop, comprising the following steps:

forming an electrically closed loop with said pipeline;

producing an alternating magnetic flux to produce, in turn, an electromagnetic field which comprises an electric field and a magnetic field;

coupling said alternating magnetic flux to said electrically closed loop for creating an alternating electromagnetic field in said electrically closed loop;

measuring at least one parameter of said electromagnetic field over at least a plurality of portions of the length and perimeter of said pipeline in said electrically closed loop;

obtaining a distribution function of at least one parameter of said electromagnetic field in said electrically closed loop; and evaluating the state of said pipeline from said distribution function.

2. A method as claimed in claim 1, wherein the operation of measuring is performed inside said pipeline.

3. A method as claimed in claim 1, wherein the operation of measuring is performed on the external surface of said pipeline.

4. A method as claimed in claim 1, wherein said pipeline includes ferromagnetic material, and the nondestructive inspection further comprises measuring magnetic noise in said ferromagnetic material and said distribution function includes at least a distribution function of at least one magnetic noise parameter, which distribution function is indicative of the state of said pipeline.

5. A method as claimed in claim 1, wherein physical processes are caused in said pipeline as a result of electromagnetic interaction between said alternating magnetic flux and said electrically closed loop, the method further comprising said at least one parameter being at least one parameter of said physical processes and obtaining at least one distribution function of said at least one parameter of said physical processes, measuring variations with time of said at least one distribution function and evaluating the state of said pipeline from said variations with time.

6. A method as claimed in claim 2, wherein physical processes are caused in said pipeline as a result of electromagnetic interaction between said alternating magnetic flux and said electrically closed loop, the method further comprising said at least one parameter being at least one parameter of said physical processes and obtaining at least one distribution function of said parameter of said physical processes, measuring variations with time of said at least one distribution function, and evaluating the state of said pipeline from said variations with time.

7. A method as claimed in claim 3, wherein physical processes are caused in said pipeline as a result of electromagnetic interaction between said alternating magnetic flux and said electrically closed loop, the method further comprising said at least one parameter being at least one parameter of said physical processes and obtaining at least one distribution function of said at least one parameter of said physical processes, measuring variations with time of said at least one distribution function, and evaluating the state of said pipeline from said variations with time of said at least one distribution function.

8. A method as claimed in claim 4, wherein physical processes are caused in said pipeline as a result of electromagnetic interaction between said alternating magnetic flux and said electrically closed loop, the method further comprising said at least one parameter being at least one parameter of said physical processes and obtaining at least one distribution function of said at least one parameter of said physical processes, measuring variations with time of said at least one distribution function and evaluating the state of said pipeline from said variations with time.

9. A method for nondestructive inspection of a pipeline incorporated in an electrically closed loop, comprising the following steps:
   forming an electrically closed loop including said pipeline;
   producing an alternating magnetic flux to produce, in turn, an electromagnetic field;
   coupling said alternating magnetic flux to said electrically closed loop which incorporates said pipeline for creating a zone of electromagnetic interaction between said alternating magnetic flux and said electrically closed loop;
   measuring at least one parameter of said electromagnetic field over a plurality of portions of a surface of said pipeline;
   obtaining a distribution function of said at least one parameter of said electromagnetic field in said electrically closed loop; and
   evaluating the state of said pipeline from said distribution function.

10. A method as claimed in claim 9, wherein physical processes are caused in said pipeline as a result of electromagnetic interaction between said alternating magnetic flux and said electrically closed loop, the method further comprising said at least one parameter being at least one parameter of said physical processes and obtaining at least one distribution function of said at least one parameter of said physical processes, measuring variations with time of said at least one distribution function, and evaluating the state of said pipeline from said variations with time.

11. A device for nondestructive inspection of a portion of a pipeline incorporated in an electrically closed loop, comprising:
   means coupled to said pipeline forming said electrically closed loop;
   a closed magnetic circuit encircling said pipeline;
   an exciting inductance coil connected to said closed magnetic circuit and effective for creating an alternating electromagnetic field in said electrically closed loop;
   an a.c. source connected to said exciting inductance;
   at least one transducer for measuring a magnetic field at a plurality of points in said electrically closed loop;
   a signal processor connected to said at least one transducer and effective to produce an output signal in response to a distribution function of at least one parameter of said magnetic field at said plurality of points; and
   a data presentation unit responsive to said output signal for indicating a state of said pipeline.

12. A device as claimed in claim 11, wherein said closed magnetic circuit includes first and second separable portions which may be split apart to permit installing said magnetic circuit encircling said pipeline and to permit removal thereof.

13. A device as claimed in claim 11, further comprising means coupled to said exciting inductance for producing a voltage in response to a condition of said exciting inductance; a voltage measuring unit receiving said voltage and producing a voltage output in response thereto; an indicator; said voltage output being connected to said indicator.

14. A device as claimed in claim 11, wherein said at least one transducer includes a transducer inductance coil coupled to a portion of said closed magnetic circuit; and said signal processor includes a unit responsive to said transducer inductance coil for integral estimation of at least one property of said closed magnetic circuit; said unit for integral estimation including a current meter connected to said transducer inductance coil and an indicator responsive to said current meter.

15. A device for nondestructive inspection of a portion of a pipeline incorporated in an electrically closed loop, comprising:
   a closed magnetic circuit encircling said pipeline;
   an exciting inductance coil connected to said closed magnetic circuit and effective for creating an alternating electromagnetic field in said electrically closed loop;
   an a.c. source connected to said exciting inductance;
   at least one transducer for measuring a magnetic field at at least one point in said electrically closed loop;
   a signal processor connected to said at least one transducer and effective to produce an output signal in response to at least one parameter of said magnetic field;
   a data presentation unit responsive to said output signal for indicating a state of said pipeline;
   at least one transducer inductance coil coupled to said closed magnetic circuit, said transducer inductance coil being effective to produce a current in proportion to a condition in said closed magnetic circuit which responds to said a.c. source;
   means for producing a reference current;
   a comparator for producing a control signal proportional to a difference between said current and said reference current; and
   said a.c. source being responsive to said control signal in a manner tending to produce a predetermined value of said difference.

16. A device as claimed in claim 11, said electrically closed circuit including ferromagnetic material, further comprising a magnetic noise processor responsive to said at least one transducer, an output of said magnetic noise processor being connected to said data presentation unit.

17. A device as claimed in claim 11, including means for disposing said at least one transducer inside said pipeline.

18. A device as claimed in claim 11, including means for disposing said at least one transducer on an external surface of said pipeline.

19. A device as claimed in claim 11, wherein said signal processor includes means for storing information and calculating its variations with time.

20. A device as claimed in claim 12, including a voltage measuring unit; an indicator; a measuring inductance coil encompassing said closed magnetic circuit; said voltage measuring unit receiving an output of said measuring inductance coil; said output of said voltage measuring unit being connected to said indicator.

21. A device as claimed in claim 12, wherein said at least one transducer includes a transducer inductance coil coupled to a portion of said closed magnetic circuit; and said signal processor includes a unit responsive to said transducer inductance coil for integral estimation of at least one property of said closed magnetic circuit; said unit for integral estimation including a current meter connected to said transducer inductance coil and an indicator responsive to said current meter.

22. A device for nondestructive inspection of a portion of a pipeline incorporated in an electrically closed loop, comprising:
  a closed magnetic circuit encircling said pipeline;
  an exciting inductance coil connected to said closed magnetic circuit and effective for creating an alternating electromagnetic field in said electrically closed loop;
  an a.c. source connected to said exciting inductance;
  at least one transducer for measuring a magnetic field at a plurality of points in said electrically closed loop;
  a signal processor connected to said at least one transducer and effective to produce an output signal in response to a distribution function of at least one parameter of said magnetic field at said plurality of points;
  a data presentation unit responsive to said output signal for indicating a state of said pipeline;
  said closed magnetic circuit including first and second separable portions which may be split apart to permit installing said magnetic circuit encircling said pipeline and to permit removal thereof;
  at least one transducer inductance coil coupled to said closed magnetic circuit, said transducer inductance coil being effective to produce a current in proportion to a condition in said closed magnetic circuit which responds to said a.c. source;
  means for producing a reference current;
  a comparator for producing a control signal proportional to a difference between said current and said reference current; and
  said a.c. source being responsive to said control signal in a manner tending to produce a predetermined value of said difference.

23. A device as claimed in claim 12, said electrically closed circuit including ferromagnetic material, further comprising a magnetic noise processor responsive to said at least one transducer, an output of said magnetic noise processor, being connected to said data presentation unit.

24. A device as claimed in claim 12, including means for disposing said at least one transducer inside said pipeline.

25. A device as claimed in claim 12, including means for disposing said at least one transducer on an external surface of said pipeline.

26. A device as claimed in claim 15, including means for disposing said at least one transducer inside said pipeline.

27. A device as claimed in claim 15, including means for disposing said at least one transducer on an external surface of said pipeline.

28. A device as claimed in claim 16, including means for disposing said at least one transducer inside said pipeline.

29. A device as claimed in claim 16, including means for disposing said at least one transducer on an external surface of said pipeline.

30. A device as claimed in claim 17, including means for disposing said at least one transducer on an external surface of said pipeline.

* * * * *